United States Patent [19]
Samuelson et al.

[11] Patent Number: 5,961,043
[45] Date of Patent: Oct. 5, 1999

[54] SUPPORTING DEVICE FOR DISPENSING VOLATILE MATERIAL

[75] Inventors: Leon C. Samuelson, Racine; James F. Kimball, Caledonia, both of Wis.; Cristopher M. Shiffler, Camden, Mich.; David J. Houser, Racine, Wis.

[73] Assignee: S. C. Johnson & Son, Inc., Racine, Wis.

[21] Appl. No.: 09/105,486

[22] Filed: Jun. 26, 1998

[51] Int. Cl.⁶ .................................................. A24F 25/00
[52] U.S. Cl. ................................. 239/54; 239/56; 239/57; 206/806; 206/486
[58] Field of Search ..................... 239/53–59; 206/45.24, 206/806, 486

[56] References Cited

U.S. PATENT DOCUMENTS

| | | | |
|---|---|---|---|
| 1,782,919 | 11/1930 | Feldman | 239/59 |
| 2,353,075 | 6/1944 | Brownstein | 239/57 |
| 2,431,924 | 12/1947 | Dunaway . | |
| 2,626,833 | 1/1953 | Valentine | 299/20 |
| 2,765,579 | 10/1956 | Gordon | 239/55 |
| 2,809,863 | 10/1957 | Curran . | |
| 2,878,061 | 3/1959 | Saeks . | |
| 2,896,853 | 7/1959 | Curran . | |
| 3,066,843 | 12/1962 | Johnson . | |
| 3,424,380 | 1/1969 | Curran . | |
| 3,784,102 | 1/1974 | Stults | 239/36 |
| 3,899,080 | 8/1975 | Brunda | 206/531 |
| 3,921,805 | 11/1975 | Compere | 206/532 |
| 4,145,001 | 3/1979 | Weyenberg et al. . | |
| 4,155,500 | 5/1979 | Dutcher | 239/59 |
| 4,157,787 | 6/1979 | Schwartz . | |
| 4,158,440 | 6/1979 | Sullivan . | |
| 4,161,283 | 7/1979 | Hyman . | |
| 4,285,468 | 8/1981 | Hyman . | |
| 4,583,686 | 4/1986 | Martens et al. . | |
| 4,634,614 | 1/1987 | Holzner . | |
| 4,653,644 | 3/1987 | Sullivan et al. | 206/538 |
| 4,722,477 | 2/1988 | Floyd | 239/36 |
| 4,804,142 | 2/1989 | Riley | 239/56 |
| 4,821,884 | 4/1989 | Griffin et al. . | |
| 4,839,144 | 6/1989 | Martin | 239/57 |
| 4,849,606 | 7/1989 | Martens et al. . | |
| 5,115,976 | 5/1992 | Weiss et al. . | |
| 5,316,148 | 5/1994 | Neumann et al. . | |
| 5,390,794 | 2/1995 | Vulpitta | 206/806 |
| 5,518,790 | 5/1996 | Huber et al. | 428/35.2 |
| 5,593,025 | 1/1997 | Feibelman | 206/806 |
| 5,711,955 | 1/1998 | Karg . | |

FOREIGN PATENT DOCUMENTS

| | | |
|---|---|---|
| 081 791 | 6/1983 | European Pat. Off. . |
| 495 631 | 7/1992 | European Pat. Off. . |
| 645081 | 3/1995 | European Pat. Off. . |
| 1568938 | 5/1969 | France . |
| 1574108 | 7/1969 | France . |
| 2262631 | 9/1975 | France . |
| 2585954 | 2/1987 | France . |
| 2589065 | 4/1987 | France . |
| 1042851 | 11/1958 | Germany . |
| 4406581 | 9/1995 | Germany . |
| 2161383 | 1/1986 | United Kingdom . |
| 1053550 | 9/1988 | United Kingdom . |
| 84/02654 | 7/1984 | WIPO . |
| 97/22370 | 6/1997 | WIPO . |

*Primary Examiner*—Andres Kashnikow
*Assistant Examiner*—Dinh Q. Nguyen

[57] ABSTRACT

A device supports and dispenses volatile materials. The device is self-supporting and has a tent-like configuration. It can be hung from a bar. One of its side panels is connected to another by a tab and slot, or tab and pocket, arrangement above a base. The base connects the side panels. There is a reservoir for dispensing the volatile material which is mounted on one of the side panels, with a rear of the reservoir being positioned between two of the panels above the base.

14 Claims, 11 Drawing Sheets

SUPPORTING DEVICE FOR DISPENSING VOLATILE MATERIAL

CROSS-REFERENCE TO RELATED APPLICATIONS

Not applicable

STATEMENT REGARDING FEDERALLY SPONSORED RESEARCH OR DEVELOPMENT

Not applicable

BACKGROUND OF THE INVENTION

The present invention relates to devices for dispensing volatile materials. More particularly, it relates to a dispensing device which is both self-standing and suitable to be hung from a closet clothes bar.

Bowls for dispensing insecticidal and/or repellent vapors are disclosed in U.S. Pat. No. 5,711,955 to Karg. In this application there is shown a container in the form of a bowl with a vapor permeable rear which is supported by cardboard packaging folded in two. The bowl projects through one of the resulting cardboard panels. A flange of the bowl is trapped between the cardboard panels until the device is activated by removing a cover strip from the rear of the bowl. The Karg disclosure requires that a removable portion of the rear card be removed to gain access to the back of the bowl for activation or that, alternatively, an opening be left in the rear card sufficiently large to allow direct access. Either arrangement leaves the activated surface of the bowl uncovered and exposed to contact with clothing or other materials that might brush against the activated surface.

In WO 97/22370 (to Harries) a device is disclosed for dispensing volatile material from a dispensing reservoir that is mounted through a sheet. The sheet also has a hanger portion for hanging the dispensing system on a closet clothes bar during use. Two such devices are attached together during retail display, with a tear line and a mounting hole therebetween.

These prior art devices are somewhat limited in how they can be used. For example, in some rooms there may not be a desirable hanging bar. In other rooms it may be aesthetically undesirable to use the reservoir by itself, or with only a cardboard frontal mounting (without some form of covering of the exposed rear of the reservoir).

It can therefore be seen that a need exists for an improved supporting device for such dispensers.

BRIEF SUMMARY OF THE INVENTION

In one embodiment the invention provides a device for dispensing volatile material. There are first and second side panels and a base joining them to provide a platform to support the device in a tent configuration, optionally allowing it to stand upon a shelf or similar surface. The second side panel has a tab extending therefrom, and there is a means to capture the tab associated with the first side panel.

One such associated means is a slot in the first side panel. Another is a pocket formed between the first side panel and a third panel that lies against the first panel.

There is also an opening in one of the side panels (preferably the first side panel). A reservoir of volatile material is mounted in that opening.

In one embodiment, the tab is in the form of a laterally extending hook, an upper portion of the first side panel is in the form of a hanger hook, and there is a vent opening through a side panel.

The tab can be formed by tearing it away from a hanger. Alternatively, the tab can have been formed by tearing a strip away from it. Also, the tab can have previously been secured to a portion of the first side panel via an adhesive (e.g. when on display at a retail store).

In another preferred form the base includes at least one vent opening. Such vent openings permit circulation of air behind the reservoir in the tent.

Two of such devices can have been previously linked in a side-by-side relationship along a tear line with a mounting hole between them adjacent the tear line.

In another aspect the invention provides a blank for forming the above device. There is a first side panel having a hanger at one end and a first opening for mounting the reservoir therein. In a preferred form, the first side panel has a slot formed between the hanger and the first opening. A base section is linked to the first side panel along a first fold line.

A second side panel is linked to the base section at a second fold line opposite the first fold line. The second side panel has means for creating a tab, or already has a tab, on a portion of the second side panel opposite the second fold line.

The invention provides a way of displaying such devices at retail locations where the opening tab of the reservoir is securely hidden from view. This helps reduce the incidence of customers attempting to sample the smell at retail.

When it is appropriate to use the product (e.g. by a consumer at home), the rear of the reservoir can be exposed by freeing one side panel from the other, allowing the two panels to be unfolded into an open position. A cover is then removed from the back of the reservoir so vapors can escape from the reservoir. The two side panels can then be re-attached to create a tent-like housing that surrounds the back of the reservoir.

The tent permits the dispenser to be self-standing, allowing a user to set it upright upon a shelf or other similar surface without the need for a structure from which to hang the dispenser. It also incorporates an integral hanger so that it can be hung in closets or the like.

Advantages of the invention (including providing blanks to form such devices) will be apparent from the description which follows. In the detailed description below, a preferred embodiment of the invention is described with reference to the accompanying drawings. The embodiment does not represent the full scope of the invention. Rather the invention may be employed in other embodiments. Reference should therefore be made to the claims herein for interpreting the breadth of the invention.

DETAILED DESCRIPTION

Referring to FIGS. 1–7, a first such device (shown generally at 10) has a first side panel 12, a second side panel 14, and a base 16 made of two panels 18 and 19. The base 16 may be generally flat, as is shown in the figures, or it may accordion upwardly, which is preferred as adding to the rigidity of the resulting structure. A bowl-like reservoir 20 contains a volatile material and is mounted on the device. A hanger section 24 permits the device to be hung from a closet clothes bar (not shown). This is an especially desirable position when the reservoir contains a moth repellent or other volatile insect control material for killing or for repelling or otherwise altering the behavior of insects.

Figures 1, 2, 4:
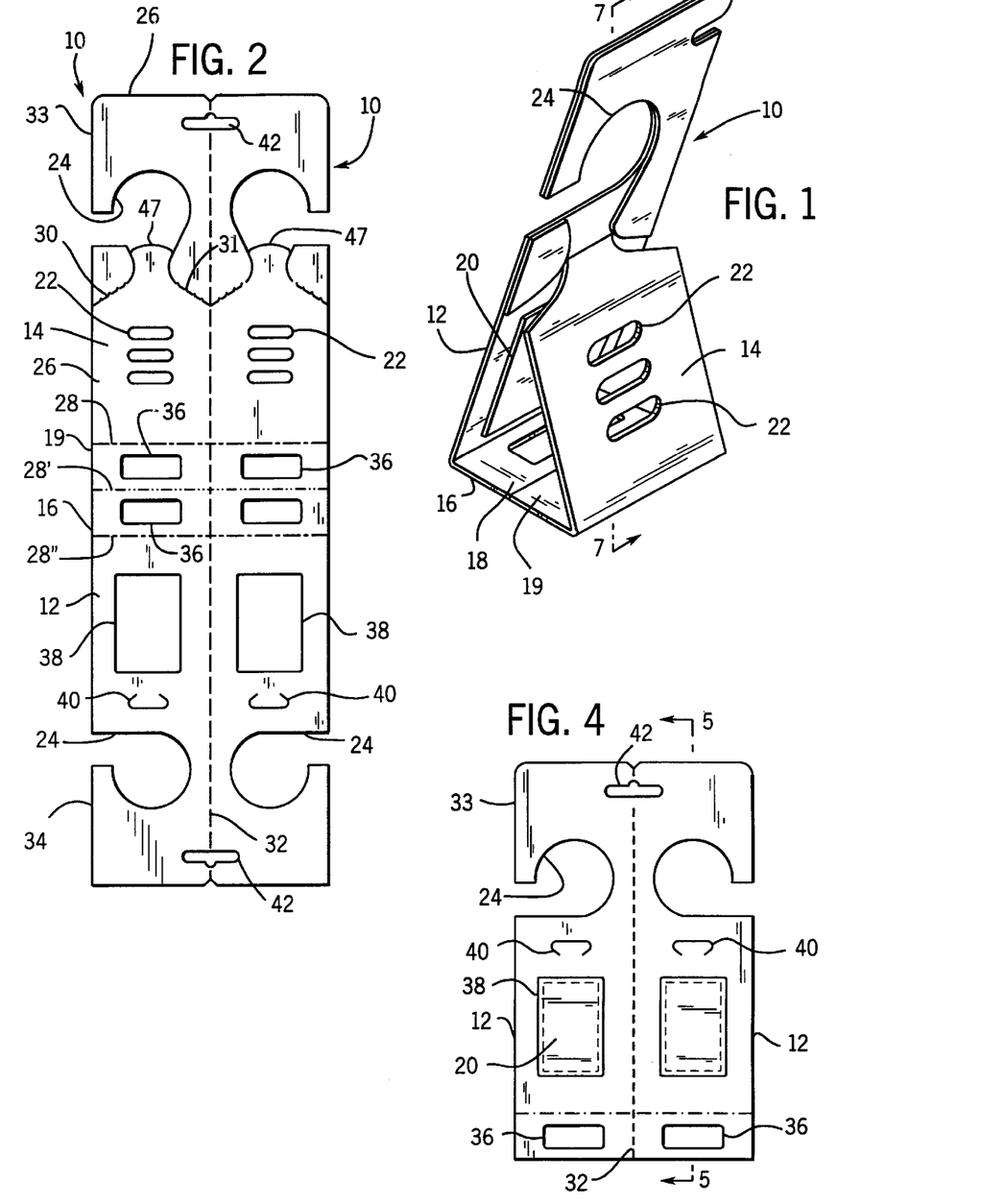
FIG. 1 is a top perspective view illustrating a device of the present invention.
FIG. 2 is a plan view of a blank for use in constructing the FIG. 1 device.
FIG. 4 is a side view of the FIG. 2 blank folded in half and assembled with a reservoir.

As seen in FIG. 2, two of the devices 10 can be formed from a single blank 26 of card material. Each has fold lines 28, 28' and 28" defining base panels 18 and 19.

Preferably, there are vent openings 22 in the second side panel 14 as well as tear lines 30 and 31, which allow the second side panel 14 to be separated from the second hanger 33. Additional vent openings 36 are provided in the base panels 18 and 19. The large rectangular window opening 38 is disposed in the first panel 12 (or alternatively it may be on the second panel 14) for receiving the reservoir.

A slot 40 is cut through the first side panel 12 for capturing tab 47. There is also a mounting hole 42 which allows for hanging two linked devices from a retail display device. After purchase, the devices 10 can be severed from each other along tear line 32.

Figure 3:
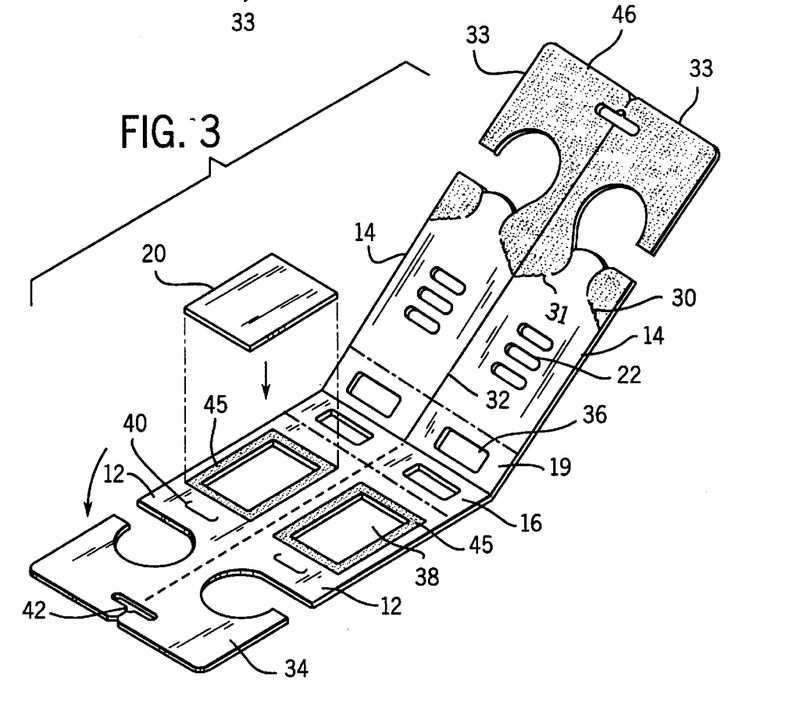
FIG. 3 is a view of the FIG. 3 blank in the process of being assembled with a reservoir.
Figure 5:
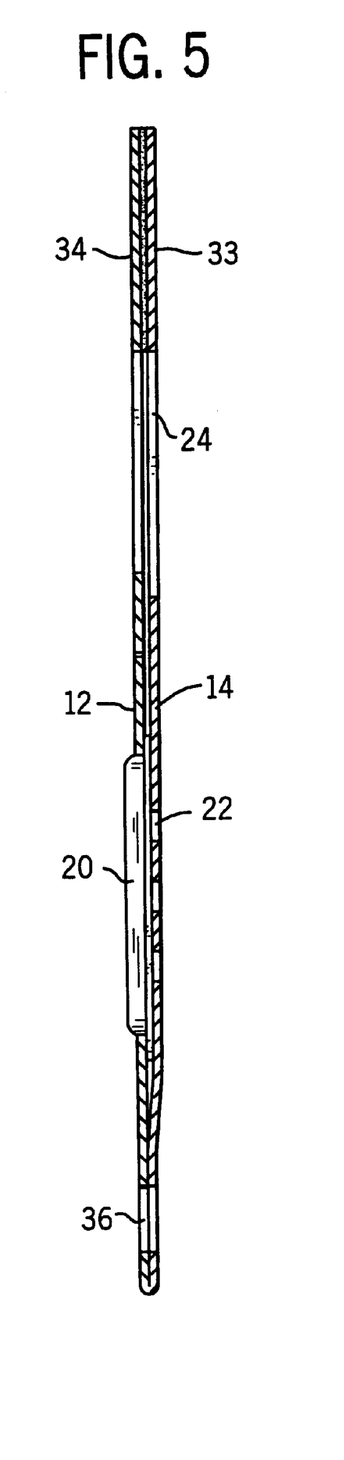
FIG. 5 is a sectional view taken along line 5—5 of FIG. 4.

FIG. 3 illustrates part of the assembly of a device of the invention. The reservoir 20 is secured into the opening 38 (e.g. by means of adhesive 45 applied around a framing edge). Adhesive 45 can also be applied to the portions 33 on a hanger portion of a panel. Portions 33 will then be placed on portions 34. The reservoir 20 is thereby attached only to one of the side panels 12 and 14, and is temporarily covered by the other of the side panels 12 and 14.

Figure 6:
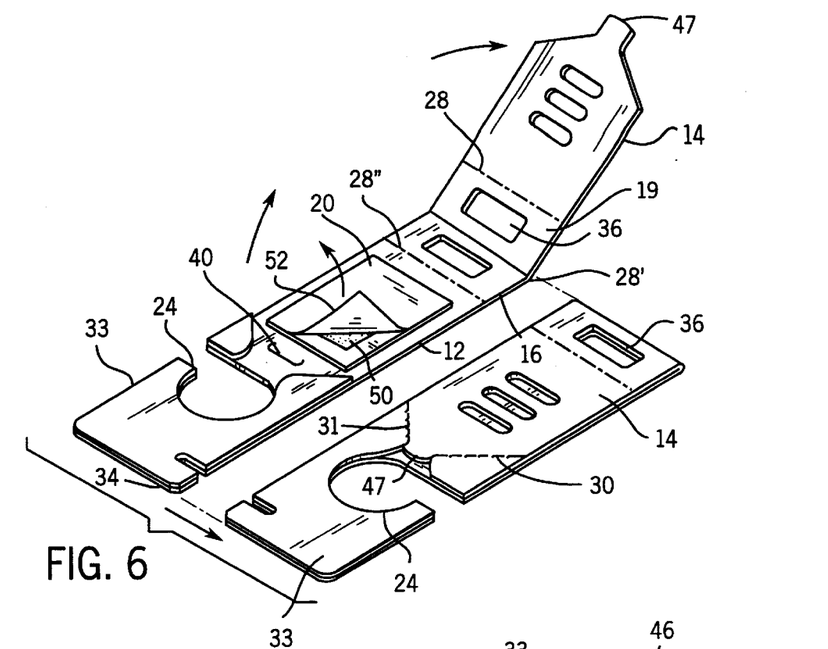
FIG. 6 is a top perspective view illustrating the device in the process of being activated.

To activate a device 10 one separates the two units as indicated in FIG. 6 by tearing along line 32. This results in the unit as shown in the right hand view of FIG. 6. Next the tab 47 is "formed" by tearing along lines 30 and 31 to separate the first panel from hanger 33. As shown on the left side of FIG. 6, this allows access to the back side of reservoir 20. An advantage of this embodiment (and of certain of the alternative embodiments described below) is that no portion of the first or second panel need be torn off or discarded in this separation process, thus avoiding the creation of loose scraps or trash that a user must dispose of.

Figure 7:
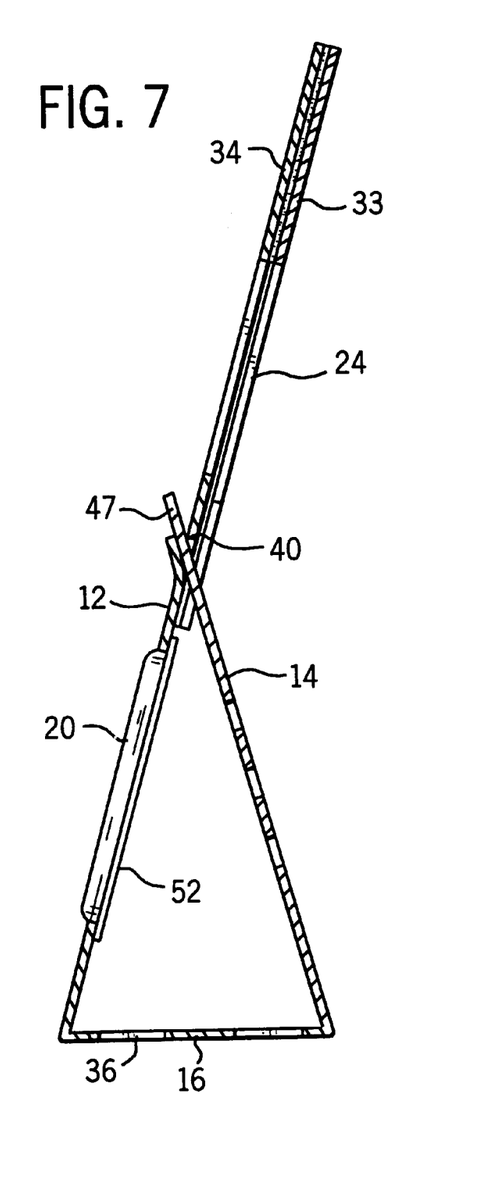
FIG. 7 is a sectional view taken along line 7—7 of FIG. 1.
Figure 8:
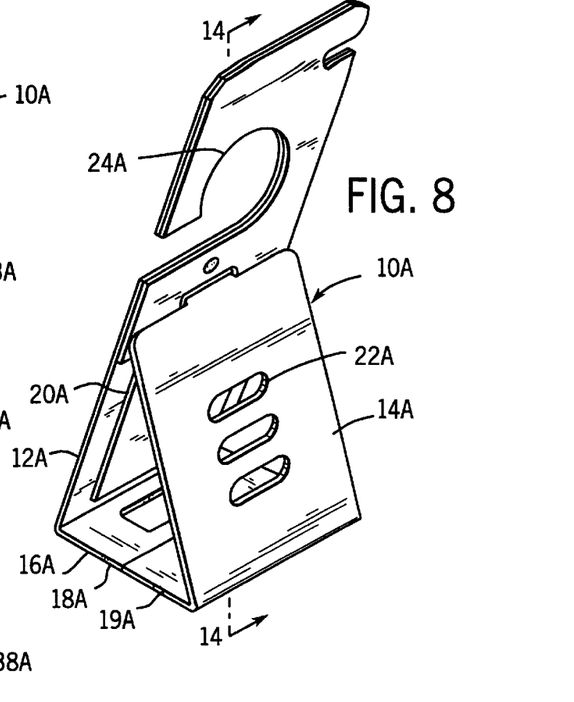
FIGS. 8, 15 and 22 are views similar to FIG. 1, albeit showing three alternative embodiments.
Figure 9:
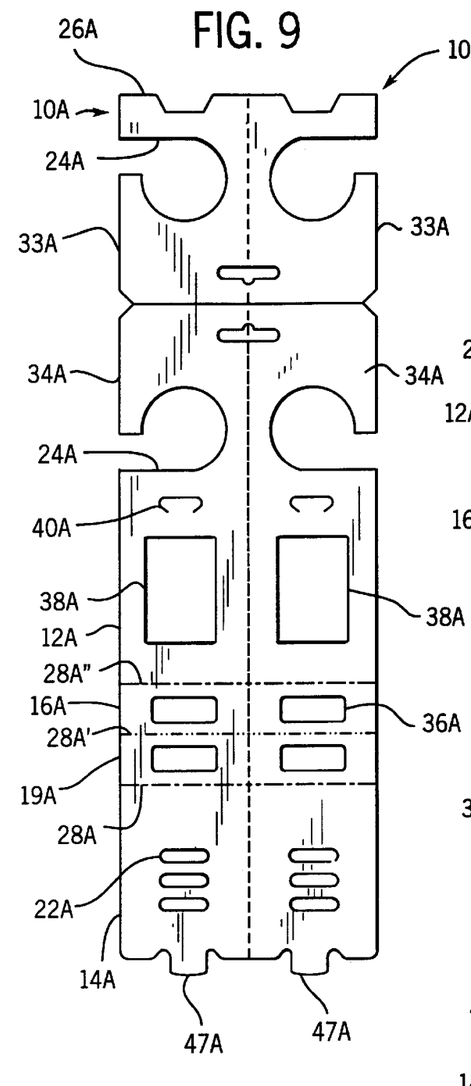
FIGS. 9, 16 and 23 are views similar to FIG. 2, albeit showing the three alternative embodiments.
Figure 10:
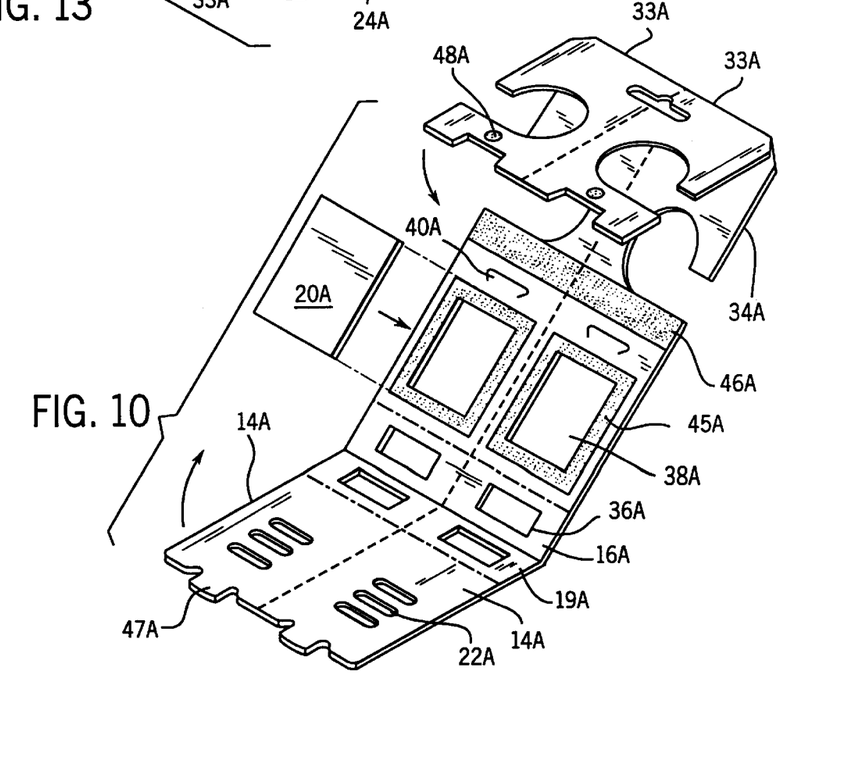
FIGS. 10, 17 and 24 are views similar to FIG. 3, albeit showing the three alternative embodiments.
Figure 11:
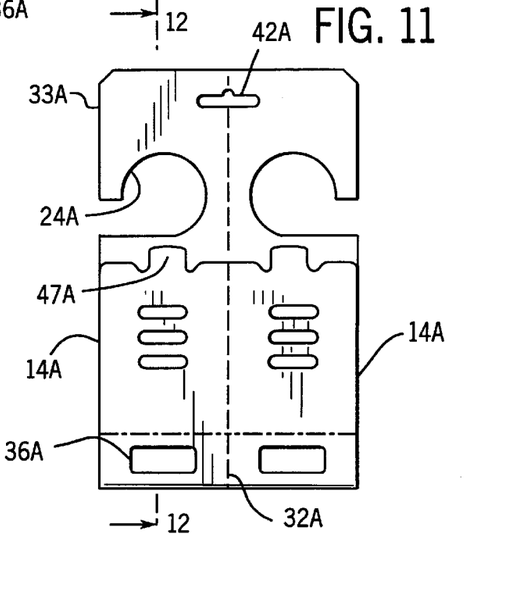
FIGS. 11, 18 and 25 are views similar to FIG. 4, albeit showing the three alternative embodiments.
Figures 12, 14:
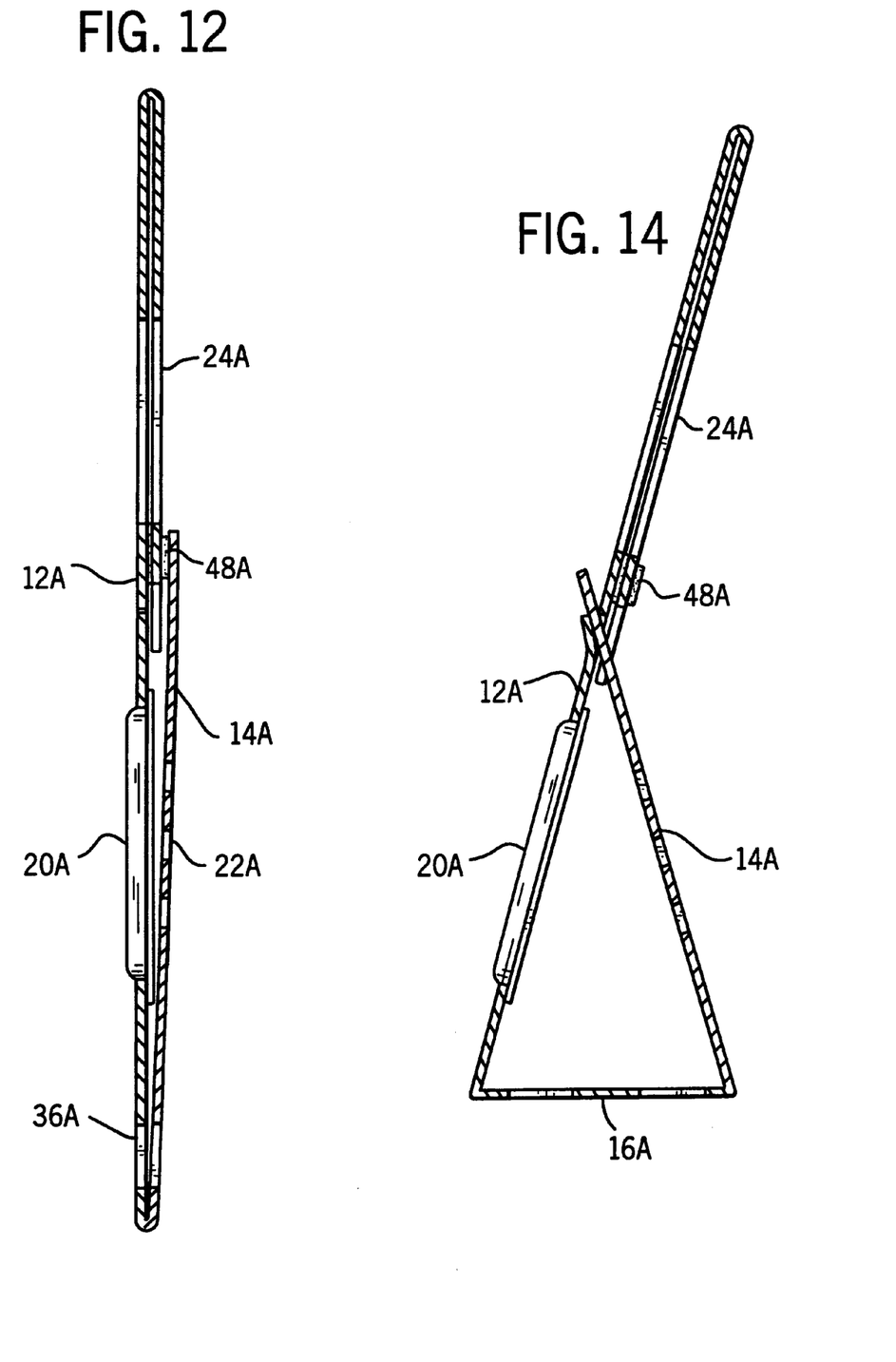
FIGS. 12, 19 and 26 are sectional views similar to FIG. 5, albeit showing the three alternative embodiments.
FIGS. 14, 20 and 28 are sectional views similar to FIG. 7, albeit showing the three alternative embodiments.

Removal of an impermeable layer 52 permits volatile material 50 to escape through an exposed, volatile-permeable wall. Subsequently, the device will be folded along fold lines 28' and 28" with the tab 47 inserted through the slot 40 to result in the tent-like device 10 (as shown in FIGS. 1 and 7).

The reservoir 20 may be similar to those described in U.S. Pat. Nos. 4,145,001 or 4,849,606 (each of which is hereby incorporated by reference as if fully set forth herein), or may be similar to those described in WO 97/22370. It can be molded from thermoplastic polymer of the type used in conventional blister packs. The volatile material can be present in the reservoir in a carrier in which it is dissolved or dispersed. The carrier may be a relatively viscous liquid. Alternatively, the carrier can be a gel or a card impregnated with the volatile material.

The volatile material is preferably an insecticide, insect repellent, or other insect control material (e.g., lavendin oil or a permethrin insecticide), or a perfume, or a combination of an insect control material and a perfume. The device of the present invention is particularly useful for insect control materials that should not contact human skin.

Where a liquid is used in the reservoir, the dispensing portion of the reservoir may be a sheet of material which allows volatile material to pass through but retains the liquid. Other layers that are impermeable to volatile materials and thus are suitable for sealing the reservoir are known to those skilled in the art. Such layers are known that are relatively thick plastic materials or that contain metal, e.g., aluminum, which may be combined with a polymer layer.

Reservoirs or chambers containing volatile material, together with a dispensing portion that is a polymer wall attached to the reservoir 20, and the removable impermeable layer 52, can be made from conventional polymers such as polyamide, polyester, polyethylene, or polypropylene. A permeable layer may be made from a polymer sold by the firm of E I du Pont de Nemours under the trade name "Surlyn". The impermeable layer 52 may be aluminum sheet. A layer of paper can be provided between the permeable layer and the impermeable layer.

As a preferred alternative, the reservoir 20 may be formed from a suitable plastic, of which an example is an acrylonitrile copolymer sold under the trade name "Barex". A thin layer of polyethylene may be glued to the acrylonitrile copolymer to enable further layers to be heat sealed to the reservoir to close it. The reservoir may be closed by a laminate of ethylene/ethyl acrylate copolymer membrane, paper, low density polyethylene or "Surlyn" polymer, aluminum foil, and polyester. The low density polyethylene enables the aluminum foil to adhere to the paper. The aluminum foil, strengthened by the polyester, provides an impermeable layer. When using ethylene/ethyl-acrylate copolymer, it is desirable to use non-polar volatile materials as the volatile material.

A substantially flat and rigid blank 26 may be formed from one or more layers of synthetic polymer, e.g., thermoplastic polymer. However, it is preferred that the blank is formed from one or more layers of card formed from wood pulp or similar cellulosic fiber.

Alternative embodiments 10A, 10B and 10C are depicted in FIGS. 8–27, respectively, with similar numbers indicating similar components except with the suffix "A", "B" and "C". One of the major differences between embodiment 10A and 10 is that the hanger 33A is connected to hanger 34A. They are then glued together along portion 46A. Another difference is the initial attachment of the tabs 47A to the hanger 33A is by adhesive.

Figure 13:
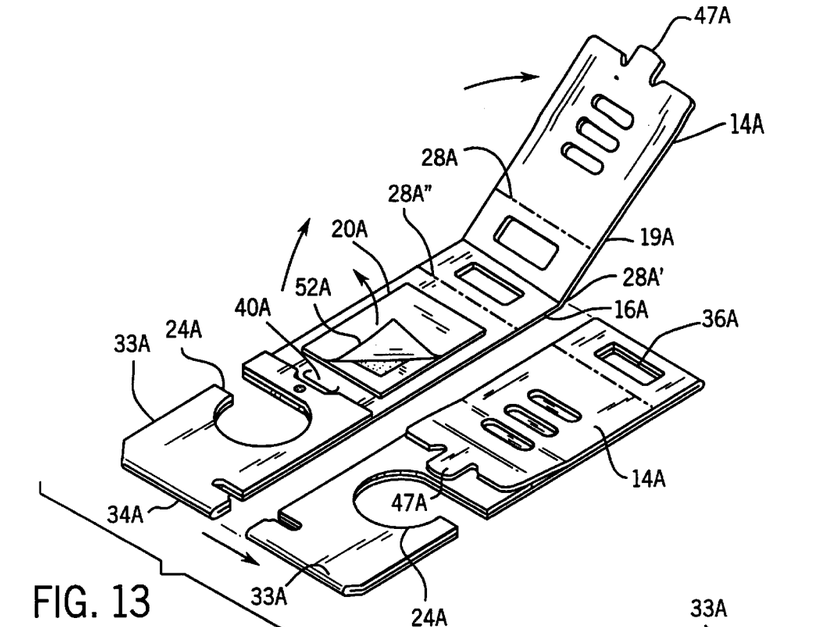
FIGS. 13 and 27 are views similar to FIG. 6, albeit showing two alternative embodiments.
Figures 15, 16, 17:
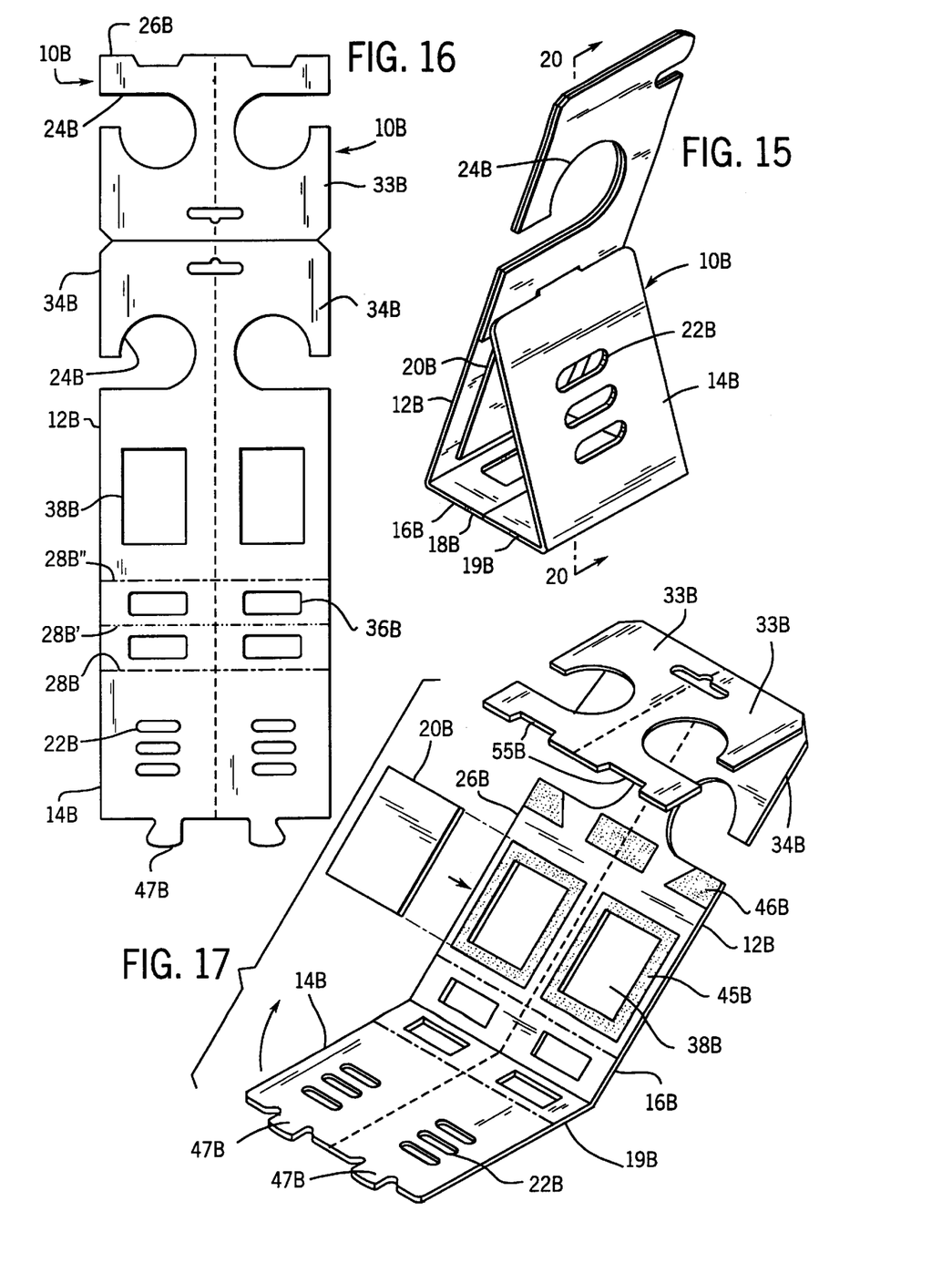

The assembled unit 10A will then appear as in the right hand portion of FIG. 13. To activate the unit, the tab 47A is torn from the hanger and first side panel 12A as previously described in conjunction with unit 10A.

Figures 18, 19, 20, 21:
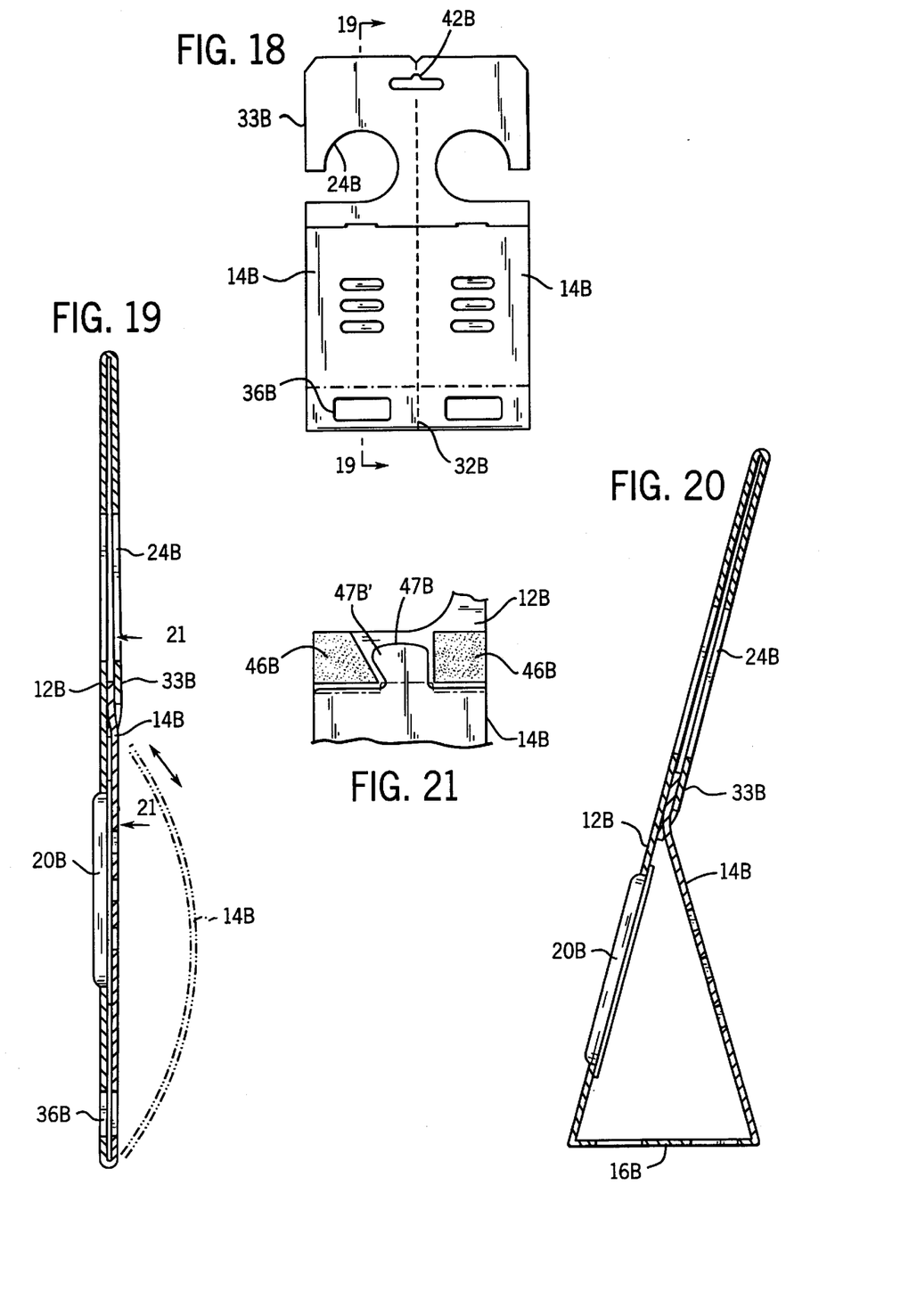
FIG. 21 is a sectional view taken along line 21—21 of FIG. 19.
Figure 22:
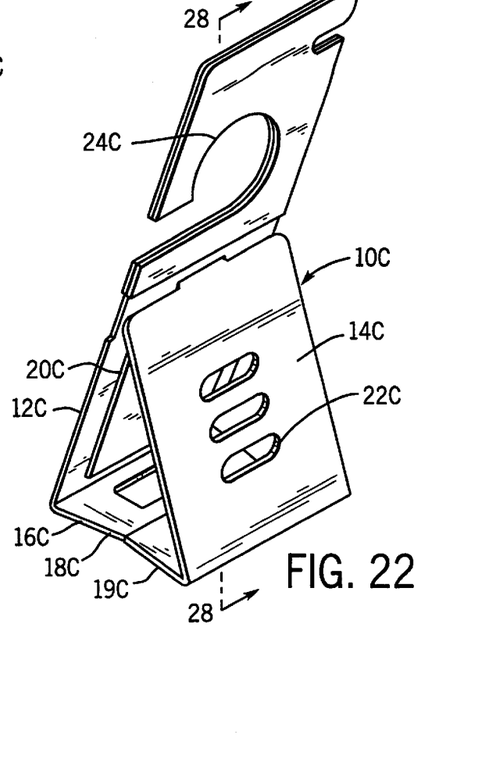
Figure 23:
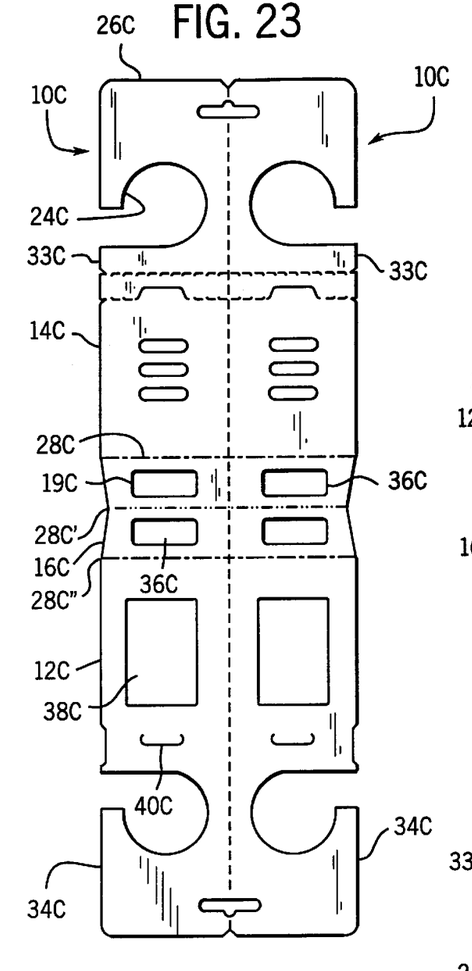
Figure 24:
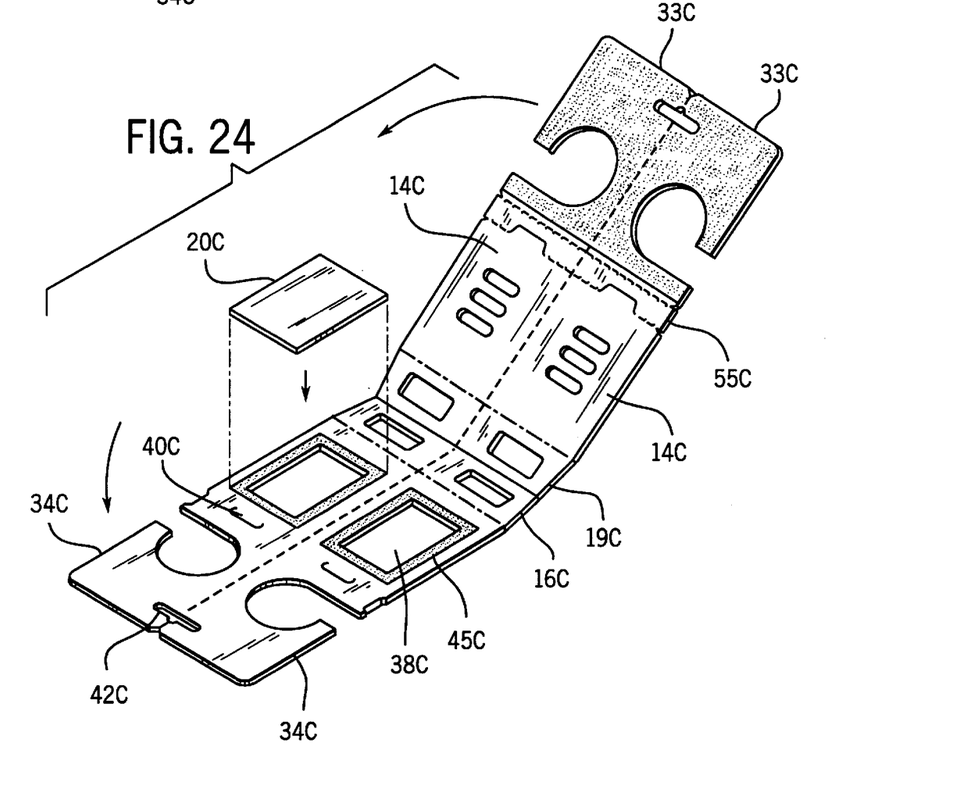
Figure 25:
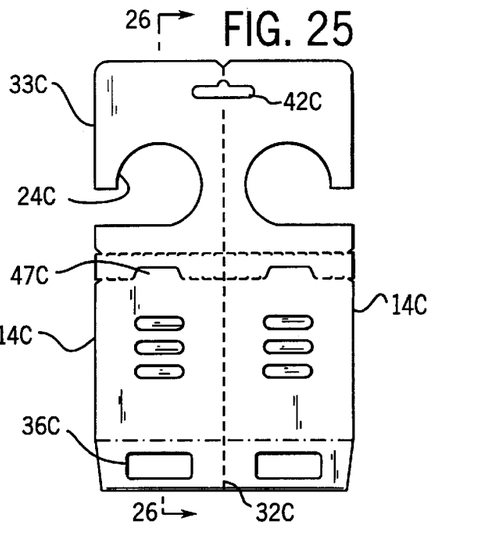
Figure 26:
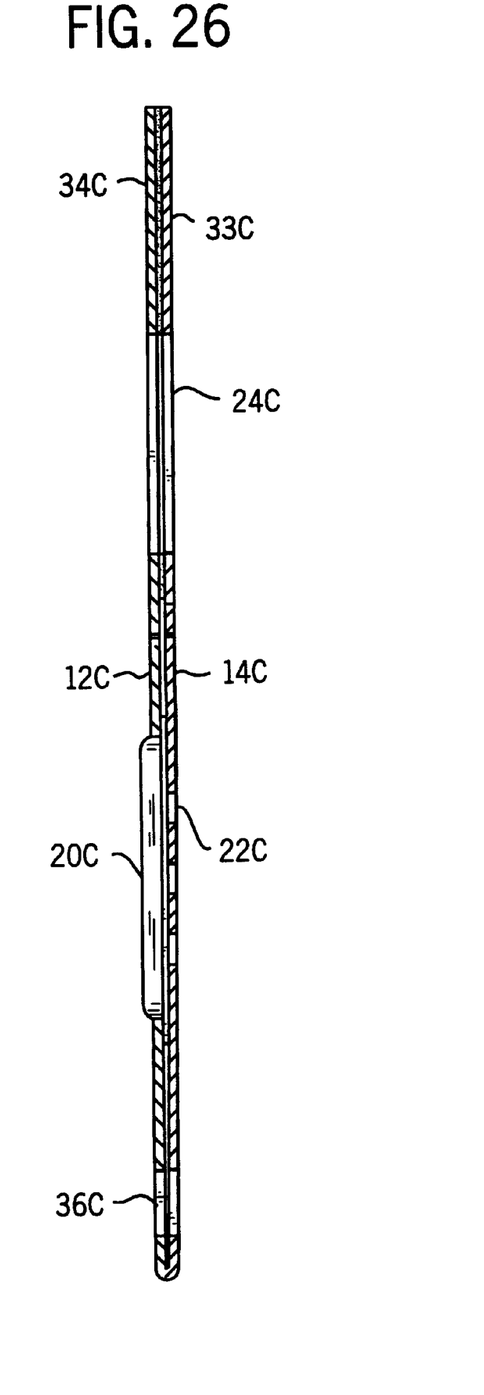
Figure 27:
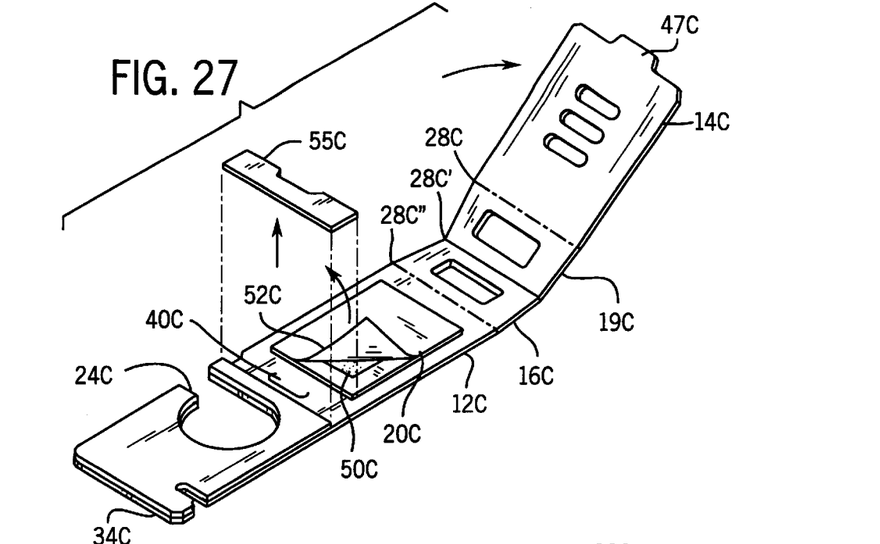
Figure 28:
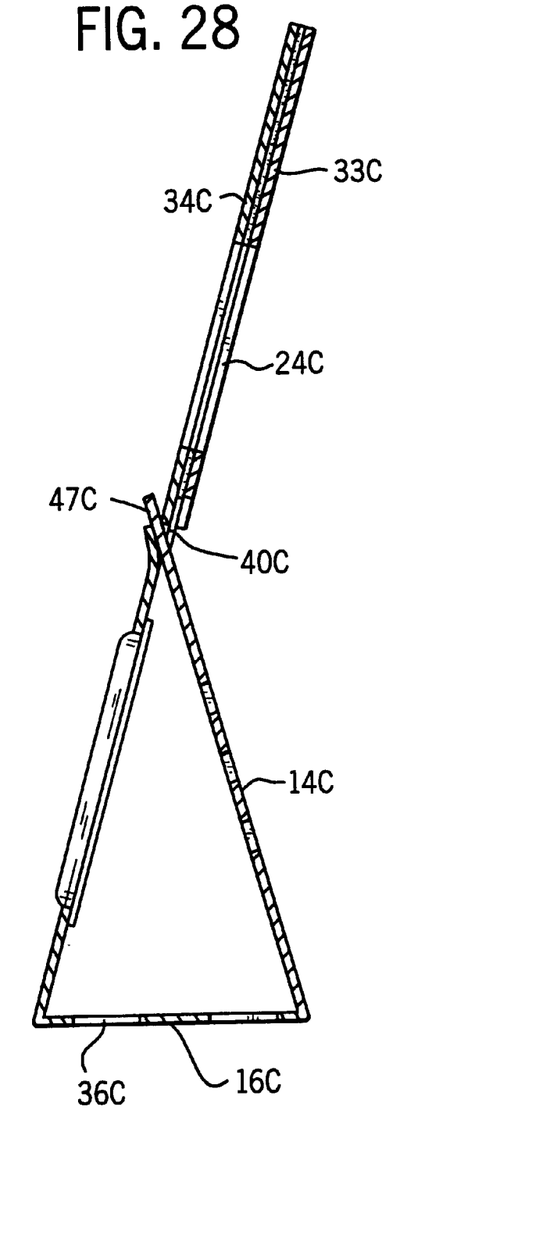

Embodiment 10B resembles more closely embodiment 10A in the adjacent placement of the hanger portions 33B and 34B. The difference between this embodiment 10B and embodiments 10A and 10 is that there is no slot such as 40A and 40. Instead the adhesive 46B does not extend completely laterally across the blank 26B. There are cutouts 55B to accommodate the tabs 47B between the hanger portions 33B and 34B as seen in FIG. 21. Note also the hooks 47B which aid in the retention of the tab, but make removal very difficult when the device is in the FIG. 18 two device configuration.

Embodiment 10C resembles mostly embodiment 10 in that the hanger portions 33C and 34C are on opposite ends of the blank 26C. A difference between this and the previous embodiments is that there is a tear strip 55C disposed between hanger portion 33C and panel 14C.

An important feature of the devices 10, 10A, 10B and 10C is that a dispensing unit is provided which is self-supporting, but which can also be hung (such as from a support rail). The positioning of the side panels and base in a tent shape, and the use of vent openings, allows air to circulate past the reservoir opening.

While specific embodiments have been shown, other modifications can be made within the scope of the invention. For example, while it is convenient to have two devices formed from a single blank, if desired a blank for a single unit or more than two units could be provided.

Furthermore, the blanks may initially be formed in front and back pieces, the two pieces, separated at, for example, the region of fold line 28' of FIG. 2. Provision may then be made for securing the front and back pieces at the fold line 28' at a convenient time in the manufacture of the assembled device 10 (e.g. by adhesive, tape, staple or other means). In fact, this arrangement may be preferred for manufacturing layouts for which long blanks, such as that of FIG. 2, are inconvenient.

INDUSTRIAL APPLICABILITY

We disclose a device which can dispense volatile materials such as insecticide from multiple positions.

We claim:

1. A device for dispensing volatile material, comprising:
   a. first and second side panels;
   b. a base joining the first and second side panels so as to provide a platform to support the device in a tent configuration;
   c. the second side panel having a tab extending therefrom;
   d. means to capture the tab associated with the first side panel;
   e. a first opening through one of the side panels; and
   f. a reservoir of volatile material, the reservoir mounted in said first opening.

2. The device of claim 1, wherein the capturing means is a slot through the second side panel.

3. The device of claim 1, wherein there is a third panel linked to the first side panel that lies against the first side panel and the capturing means is a pocket formed between the first side panel and the third panel.

4. The device of claim 3, wherein the tab is in the form of a laterally extending hook.

5. The device of claim 1, wherein an upper portion of the first side panel is in the form of a hanger hook.

6. A device of claim 1, wherein there is a vent opening through a side panel.

7. The device of claim 1, wherein the tab is formed by tearing it away from a hanger panel.

8. The device of claim 1, wherein the tab is formed by tearing a strip away from the tab.

9. The device of claim 1, wherein the base includes at least one vent opening.

10. The device of claim 1, wherein two of such devices had previously been linked in a side-by-side relationship along a tear line.

11. The device of claim 10, wherein when said two devices were so linked they formed a mounting hole between them adjacent the tear line.

12. A blank for the device of claim 1 comprising:
    a. a first side panel having a hanger at one end and an opening for mounting a reservoir therein;
    b. a base section linked to the first side panel along a first fold line opposite the hanger; and
    c. a second side panel linked to the base section at a second fold line opposite the first fold line, the second side panel having means for creating a tab, or a tab, on a portion of the second side panel opposite the second fold line.

13. The blank of claim 12, wherein the first side panel has a slot formed between the hanger and the first opening.

14. The blank of claim 13 separated into two formable blank portions, a front portion including the first side panel and a back portion including the second side panel, parts or all of the base section accompanying one of the front and back portions.

\* \* \* \* \*